(12) United States Patent
Fremy et al.

(10) Patent No.: US 7,339,083 B2
(45) Date of Patent: Mar. 4, 2008

(54) CATALYTIC METHOD OF PRODUCING ALKYL MERCAPTANS BY ADDING HYDROGEN SULPHIDE TO AN OLEFIN

(75) Inventors: Georges Fremy, Sauveterre de Bearn (FR); Nadine Essayem, Saint-Just Chaleyssin (FR); Michel Lacroix, Lyons (FR); Elodie Zausa, Targon (FR)

(73) Assignee: Arkema France, Colombes (FR)

( * ) Notice: Subject to any disclaimer, the term of this patent is extended or adjusted under 35 U.S.C. 154(b) by 304 days.

(21) Appl. No.: 10/528,901

(22) PCT Filed: Sep. 23, 2003

(86) PCT No.: PCT/FR03/02789

§ 371 (c)(1),
(2), (4) Date: Dec. 20, 2005

(87) PCT Pub. No.: WO2004/029005

PCT Pub. Date: Apr. 8, 2004

(65) Prior Publication Data
US 2006/0111591 A1    May 25, 2006

(30) Foreign Application Priority Data
Sep. 25, 2002    (FR) .................. 02 11923

(51) Int. Cl.
*C07C 319/04* (2006.01)
*C07C 321/04* (2006.01)
*C07B 45/06* (2006.01)

(52) U.S. Cl. ............... 568/72; 568/69; 568/70; 568/73

(58) Field of Classification Search .......... 568/72, 568/73
See application file for complete search history.

(56) References Cited

U.S. PATENT DOCUMENTS

| | | |
|---|---|---|
| 2,950,324 A | 8/1960 | Loev et al. |
| 2,951,875 A | 9/1960 | Loev et al. |
| 3,036,133 A | 5/1962 | Goshorn et al. |
| 4,102,931 A | 7/1978 | Buchholz |
| 5,113,034 A | 5/1992 | Soled et al. |
| 5,420,092 A | 5/1995 | Soled et al. |
| 5,453,544 A | 9/1995 | Giacobbe |
| 6,162,952 A | 12/2000 | Cook et al. |

FOREIGN PATENT DOCUMENTS

| | | |
|---|---|---|
| EP | 0 354 460 | 4/1994 |
| RO | 114253 B * | 2/1999 |

OTHER PUBLICATIONS

A. P. Ginsberg, Inorganic Synthesis, vol. 27, published by J. Wiley and Sons (1990), p. 105-107.
N. Essayem, G. Coudurier, M. Fournier, J.C. Vedrine, Catal Lett. 34 (1995), p. 224-225.
F.R. Chen, G. Coudurier, J.F. Joly and J.C. Vedrine, J. Catal., 143 (1993), p. 617.

* cited by examiner

*Primary Examiner*—Yvonne Eyler
*Assistant Examiner*—Yevgeny Valenrod
(74) *Attorney, Agent, or Firm*—Steven D. Boyd

(57) ABSTRACT

The process for preparing a mercaptan from an olefin and hydrogen sulphide is carried out in the presence of hydrogen and a catalyst composition comprising a strong acid, such as a heteropolyacid, and at least one metal belonging to group VIII of the Periodic Table.

23 Claims, No Drawings

CATALYTIC METHOD OF PRODUCING ALKYL MERCAPTANS BY ADDING HYDROGEN SULPHIDE TO AN OLEFIN

FIELD OF THE INVENTION

The present invention pertains to the field of mercaptans (also called thiols) and relates more particularly to a catalytic process for preparing mercaptans from an olefin and hydrogen sulphide in the presence of hydrogen and a specific catalyst.

BACKGROUND OF THE INVENTION

The industrial significance of mercaptans or thiols means that many studies have been carried out for the purpose of perfecting the preparation of these compounds.

In particular a process is known which is widely employed and which implements the reaction of hydrogen sulphide with an alcohol or an olefin. In such a reaction a by-product which is obtained in particular comprises one or more thioethers, which result from secondary reactions and, primarily, from the reaction of the mercaptan (formed in the main reaction) with the starting reactant, in other words either the alcohol or the olefin, depending on the process used.

Thioethers obtained as by-products during the preparation of mercaptans are not generally of commercial significance.

It is therefore essential to improve the selectivity of the catalyst employed in the reaction, so as to increase the yield of thiol, more particularly when the latter is obtained by addition of hydrogen sulphide to an olefin, a reaction often called sulfhydration.

Methods of sulfhydration have been proposed which are directed at reacting hydrogen sulphide ($H_2S$) with an olefin under pressure in the presence of various catalysts.

Many catalysts have been proposed in the prior art, and in particular supported phosphoric acid (by U.S. Pat. No. 2,950,324), silica with small amounts of alumina (by U.S. Pat. No. 2,951,875), a synthetic zeolite (by U.S. Pat. Nos. 4,102,931 and 5,453,544) or an ion exchange resin (cf. U.S. Pat. No. 4,102,931). The ion exchange resins allow values to be obtained that are of interest for the conversion of the olefin and the selectivity to mercaptan. However, these resins undergo degradation at 100° C. and above, and are completely decomposed at 140° C. The result of this is that they do not allow the catalysis of sulfhydration reactions, which, owing to the olefin used, require a high temperature.

U.S. Pat. No. 6,162,952 describes a catalyst supported on an oxide ($TiO_2$ or $ZrO_2$) associated with an acidic $H_2SO_4$, $(NH_4)_2SO_4$ or $WO_3$ site. However, owing to the likewise-limited stability of these solids at temperature (at approximately 200° C.), this catalyst has the same drawback as before.

U.S. Pat. No. 3,036,133 describes the preparation of ethyl mercaptan and diethyl sulphide by addition of $H_2S$ to ethylene in the presence of a catalyst comprising silica or alumina activated with a heteropolyacid, or one of its alkali metal or alkaline-earth metal salts. However, this catalyst, when employed for an olefin other than ethylene, such as propene or butene for example, produces a low conversion to olefin. Moreover, the selectivity to mercaptan, and hence the yield of mercaptan, are generally insufficient.

A solid catalyst comprising a 12-phosphotungstic acid supported on silica is also described by U.S. Pat. No. 5,420,092. That document teaches, more generally, the use of a heteropolyacid in combination with a metal from group VIII, but in the distant field of the isomerization of paraffins.

DETAILED DESCRIPTION OF THE INVENTION

A new catalytic process has now been found for preparing a mercaptans from olefins and hydrogen sulphide, which employs hydrogen in the reaction stream and a specific catalyst. It has the advantage of being able to be used at a higher temperature, obtaining an improved yield for the desired mercaptan, and of maintaining a high activity for the catalyst over time.

The invention accordingly provides a process for preparing a mercaptan from an olefin and hydrogen sulphide, characterized in that it is carried out in the presence of hydrogen and a catalyst composition comprising a strong acid and at least one metal belonging to group VIII of the Periodic Table.

The combination of the hydrogen with this catalyst composition allows the activity of the catalyst to be stabilized at a high level over time and even for a relatively high use temperature. This result is all the more surprising for being obtained in a sulphurizing medium, which is known to poison the active sites of catalysts.

The strong acid which can be used in the catalyst composition is selected from the group consisting of:
  (a) one or more heteropolyacids selected from:
     (i) a compound of formula: $H_3PW_{12}O_{40}.nH_2O$, $H_4SiW_{12}O_{40}.nH_2O$ or $H_6P_2W_{18}O_{62}.nH_2O$, in which n is an integer representing the number of molecules of water of crystallization, and (for a commercial product) is generally between 0 and 30, preferably between 6 and 20;
     (ii) a potassium, rubidium, caesium or ammonium salt of at least one compound (i), or a mixture of such salts;
  (b) a sulphated zirconium oxide,
  (c) a tungstic zirconium oxide,
  (d) a zeolite, and
  (e) a cationic resin.

The heteropolyacid (i) is generally obtained by condensing two or more different oxo acids, such as phosphoric acid, silicic acid or tungstic acid. It is soluble in water or in a polar organic solvent. The compound of formula $H_3PW_{12}O_{40}.nH_2O$ is known under the name of 12-phosphotungstic or 12-tungstophosphoric acid and is available commercially. The compound of formula $H_4SiW_{12}O_{40}.nH_2O$ is known under the name of 12-tungstosilicic or 12-silicotungstic acid, and is likewise available commercially. The compound of formula $H_6P_2W_{18}O_{62}.nH_2O$ can be prepared according to the procedure described in the following reference: A. P. Ginsberg, Inorganic Synthesis, Vol. 27, published by J. Wiley & Sons (1990) pages 105-107.

The heteropolyacid (ii) is a salt obtained by partial substitution of one or more protons of the heteropolyacid (i) by the corresponding cation. It is evident to the skilled person that such substitution cannot be total without the acidity being lost. A salt of this kind is prepared from a solution of the heteropolyacid (i), to which the desired amount of the alkali metal or ammonium precursor is added. The preferred precursor is the corresponding chloride or carbonate. The precipitated salt is separated off and then dried under gentle conditions, preferably by centrifugation followed by lyophilization. One reference which may be mentioned is the following: N. Essayem, G. Coudurier, M. Fournier, J. C. Vedrine, *Catal. Lett.*, 34 (1995) pages 224-225.

The sulphated zirconium oxide (b) is prepared by impregnating sulphuric acid on a zirconium oxide support in accordance with the process described in the following reference:

F. R. Chen, G. Coudurier, J-F Joly and J. C. Vedrine, *J. Catal.*, 143 (1993) page 617.

The tungstic zirconium oxide (c) is prepared by impregnating tungsten oxide on a zirconium oxide support, in accordance with the process described in U.S. Pat. No. 5,113,034 to Soled et al.

According to a first embodiment of the process according to the invention the catalyst employed in the said process comprises as strong acid a heteropolyacid (ii), or one of the compounds (b), (c), (d) or (e). This version is preferred because, owing to the specific surface properties of a strong acid of this kind, it is generally suitable as a support. It is therefore not necessary in this case to deposit the strong acid on a support.

The catalyst composition comprises in this case:
from 90% to 99.9%, preferably from 98.5% to 99.5%, by weight of strong acid, and
from 0.01% to 10%, preferably from 0.05% to 1.5%, by weight of metal from group VIII.

According to a second embodiment the catalyst employed comprises as strong acid a heteropolyacid (i). This version is preferred owing to the particularly advantageous activity of the catalyst in the sulfhydrolysis reaction.

The catalyst composition comprises in this case:
from 10% to 60%, preferably from 25 to 50%, by weight of strong acid,
from 0.01% to 10%, preferably from 0.1% to 2%, by weight of metal from group VIII, and
from 30% to 80%, preferably from 48% to 75%, by weight of a support selected from silica $SiO_2$, alumina $Al_2O_3$, titanium dioxide $TiO_2$, zirconium oxide $ZrO_2$, and activated carbon.

According to one particularly preferred embodiment the strong acid employed in the catalyst is 12-phosphotungstic acid, preferably impregnated on silica.

The metal or metals belonging to group VIII of the Periodic Table that is or are generally included in the catalyst composition employed is or are selected from, in particular, iron, cobalt, nickel, ruthenium, rhodium, palladium, osmium, iridium, and platinum.

Preference is given to employing a metal from group VIII that is selected from palladium, ruthenium and platinum, and is especially platinum.

One particularly preferred catalyst composition is that comprising approximately 40% by weight of 12-phosphotungstic acid, 1% of platinum and 59% of silica.

The catalyst composition employed in a process according to the invention may be prepared generally as follows:
When the strong acid used is one of the compounds (i):
(1) the support is heat-treated under vacuum at a temperature of between 90 and 150° C., preferably of around 100° C., and then
(2) the support thus treated is impregnated with an aqueous or organic solution of acid pH, containing the compound (i) and an acidic precursor of the metal from group VIII, and then
(3) the solid thus obtained is dried, and then
(4) is treated with $H_2$ at a temperature of between 80 and 300° C., preferably between 180 and 250° C.

The aim of the heat treatment of step (1) is to desorb the water which may have been adsorbed in the pores of the support.

In step (2) the acidic precursor refers to a compound which in aqueous solution gives rise to a cationic or anionic complex of the said metal. Examples of such compounds, in the case of platinum, are as follows: tetraammineplatinum hydroxide, tetraammine platinum chloride, dinitrodiamineplatinum(II), or else, in the case of palladium: palladium chloride, $Pd(NH_3)_4Cl_2$, $(NH_4)_2(PdCl_4)$. Examples of such compounds further include, in the case of platinum: hexachloroplatinic acid (also called hydrogen hexachloroplatinate(IV)), ammonium tetrachloroplatinate(II), and ammonium hexachloroplatinate(IV). The list of acidic precursors is given above purely by way of illustration, without limiting the compounds which can be used as an acidic precursor by the skilled person.

In step (3) the drying may be carried out, for example, by heating the impregnated support, where appropriate under vacuum, at a temperature of generally between ambient temperature and 120° C. for a time ranging from 30 minutes to 5 hours.

The $H_2$ treatment of step (4) is advantageously carried out on the catalyst when the latter has been placed in the sulfhydrolysis reactor, and its purpose is to reduce the acidic precursor to metal from group VIII.

When the catalyst employed comprises as strong acid a heteropolyacid (ii), or one of the compounds (b), (c), (d) or (e), it may be prepared by the same process except for the fact that the heat treatment is not mandatory, and must even be suppressed or modified, depending on the characteristics of the support.

The catalyst composition described above is employed in the process for preparing mercaptan according to the invention, which comprises reacting hydrogen sulphide ($H_2S$) with an olefin in the presence of hydrogen.

This process is carried out in the gas phase, insofar as the temperature and pressure conditions utilized are such that the reactants and the products are in the gaseous state.

The hydrogen is introduced into the process in an amount corresponding to a molar $H_2S/H_2$ ratio of between 0.05 and 200, preferably between 0.1 and 100.

The olefin used as starting reactant has the general formula:

$$R_1R_2C=CR_3R_4 \qquad (I)$$

in which $R_1$, $R_2$, $R_3$, $R_4$, which are identical or different, represent a hydrogen atom or an alkyl radical of 1 to 20 carbon atoms, preferably 1 to 12 carbon atoms, which is linear or branched.

The olefin preferably used is ethylene. The sulfhydration reaction leads in this case to ethyl mercaptan (or ethanethiol).

The hydrogen sulphide is introduced into the process in an amount sufficient to produce the conversion of the olefin. Generally speaking, this amount corresponds to a molar $H_2S$/olefin ratio of between 1 and 100, preferably between 2 and 30, more preferably between 4 and 12.

The reactants described above are contacted in the presence of a charge of the catalyst composition defined above in an appropriate reaction zone under reaction conditions appropriate for producing the desired thiol.

The process is preferably implemented in a reactor which is fed continuously with the reactants, although a batch reactor may also be used.

The reaction temperature varies according to the olefin used and the desired degree of conversion, but is generally situated within a range of between 30 and 350° C., preferably between 50 and 250° C.

The pressure at which the reaction is carried out also varies within wide limits. Commonly it is situated at between atmospheric pressure and 50 bars, preferably between atmospheric pressure and 15 bars.

The contact time is generally between 1 and 50 s, preferably between 2 and 30 s.

The examples below are given purely by way of illustration of the invention, and must in no way be interpreted as constituting any limitation thereon. In these examples the abbreviation HPW corresponds to the 12-phosphotungstic acid of formula $H_3PW_{12}O_{40} \cdot nH_2O$.

EXAMPLE 1

Preparation of the Pt Catalyst and HPW, Supported on $SiO_2$

For 200 g of $SiO_2$, an aqueous solution is prepared which contains 7.5 g of hexachloroplatinic acid, of formula $H_2PtCl_6$ and 140 g of HPW (weight expressed in equivalents of anhydrous acid, i.e. with n equal to 0).

The catalyst support used is an amorphous silica having a specific (or BET) surface area of 315 $m^2 \cdot g^{-1}$, a pore diameter of the order of 12 to 14 nm and a pore volume of 1.6 $cm^3 \cdot g^{-1}$. This support is treated under vacuum beforehand at a temperature of 100° C.

The solution obtained above is impregnated onto the support thus treated under vacuum by aspiration. When impregnation of the solution has been carried out, the mixture is stirred at atmospheric pressure for 1 hour.

The product obtained is dried under vacuum at ambient temperature and is then subjected to treatment with hydrogen at a temperature of 200° C. for the purpose of reducing the platinum.

The catalyst obtained is composed of 59% by weight of $SiO_2$, 1% by weight of platinum and 40% by weight of HPW.

EXAMPLE 2

Preparation of Ethyl Mercaptan ($CH_3CH_2$—SH) from Ethylene

A micro reactor with a diameter of 15 mm is used which has a useful capacity of 5 ml and is charged with 1.2 ml (0.1 g) of the catalyst composition prepared according to example 1.

Passed through this charge per hour are 70 l of ethylene (or 3 mol), 270 l of $H_2S$ (or 12 mol) and 1700 l of $H_2$ (or 53 mol).

The pressure in the reactor is maintained at atmospheric pressure and the temperature is set at 200° C.

When the steady state has been attained, a conversion to olefin of 3.4% and a yield of the ethyl mercaptan of 3.3% are measured.

EXAMPLE 3

Preparation of Ethyl Mercaptan ($CH_3CH_2$—SH) from Ethylene—Change in the Conversion of Ethyl Mercaptan Over Time Example 2 is repeated, continuing the sulfhydratation reaction for 48 hours with the same charge of catalyst composition, and periodically (as a function of the time, expressed in hours), measuring the conversion of ethylene.

The results are collated in table 1 below.

TABLE 1

| Time (hours) | Conversion of ethylene (in %) |
|---|---|
| 1 | 4.5 |
| 2 | 4.3 |
| 20 | 3.4 |
| 48 | 3.4 |

Table 1 shows that the catalyst system prepared in example 1 and used in the presence of hydrogen according to the process of the invention processes good stability over time.

Table 1 shows that the catalyst system prepared in example 1 and used in the presence of hydrogen according to the process of the invention possesses good stability over time.

EXAMPLE 4 (COMPARATIVE)

Preparation of Ethyl Mercaptan (Et-SH) from Ethylene with a catalyst of Type $Cr_2O_3$ Supported on $Al_2O_3$ Example 2 is repeated, omitting the introduction of $H_2$ and replacing the catalyst composition of example 1 by a catalyst of type $Cr_2O_3$ supported on $Al_2O_3$ (Cr content: 19% by weight). A catalyst of this kind is often used under industrial production conditions, and is used here by way of reference.

Again in the steady state, an initial conversion of the ethylene of 1.3% and a yield of ethyl mercaptan of 1.2% are measured.

The invention claimed is:

1. Process for preparing a mercaptan comprising contacting an olefin and hydrogen sulphide, in the presence of hydrogen and a catalyst composition comprising a strong acid and at least one metal selected from group VIII of the Periodic Table.

2. Process according to claim 1, wherein the strong acid is selected from the group consisting of:
   (a) one or more heteropolyacids selected from the group $H_3PW_{12}O_{40} \cdot nH_2O$, $H_4SiW_{12}O_{40} \cdot nH_2O$ or $H_6P_2W_{18}O_{62} \cdot nH_2O$, in which n is an integer representing the number of molecules of water of crystallization, and is between 0 and 30, potassium, rubidium, caesium or ammonium salts thereof and mixtures of such salts;
   (b) a sulphated zirconium oxide,
   (c) a tungstic zirconium oxide,
   (d) a zeolite, and
   (e) a cationic resin.

3. Process according to claim 1, wherein the strong acid is selected from the group potassium, rubidium, caesium or ammonium salts or a mixture of such salts of $H_3PW_{12}O_{40} \cdot nH_2O$, $H_4SiW_{12}O_{40} \cdot nH_2O$ or $H_6P_2W_{18}O_{62} \cdot nH_2O$, in which n is an integer representing the number of molecules of water of crystallization, and is between 0 and 30, a sulphated zirconium oxide, a tungstic zirconium oxide, a zeolite, and a cationic resin.

4. Process according to claim 1, wherein the catalyst composition comprises:
   from 90% to 99.9%, by weight of strong acid, and
   from 0.01% to 10%, by weight of at least one metal from group VIII.

5. Process according to claim 1, wherein the strong acid is a heteropolyacid selected from the group $H_3PW_{12}O_{40} \cdot nH_2O$, $H_4SiW_{12}O_{40} \cdot nH_2O$ or $H_6P_2W_{18}O_{62} \cdot nH_2O$, in which n is an integer representing the number of molecules of water of crystallization, and is between 0 and 30.

6. Process according to claim 5, wherein the catalyst composition comprises:
   from 10% to 60%, by weight of strong acid,
   from 0.01% to 10%, by weight of at least one metal from group VIII, and
   from 30% to 80%, by weight of a support selected from silica $SiO_2$, alumina $Al_2O_3$, titanium dioxide $TiO_2$, zirconium oxide $ZrO_2$, and activated carbon.

7. Process according to claim 6, wherein the strong acid is 12-phosphotungstic acid.

8. Process according to one of claim 1, wherein the at least one metal is selected from iron, cobalt, nickel, ruthenium, rhodium, palladium, osmium, iridium, and platinum.

9. Process according to claim 1, wherein the at least one metal is selected from palladium, ruthenium, and platinum.

10. Process according to claim 1, wherein the at least one metal is platinum.

11. Process according to claim 1 wherein the catalyst composition comprises approximately 40% by weight of 12-phosphotungstic acid, 1% of platinum and 59% of silica.

12. Process according to claim 1, wherein the hydrogen is introduced in an amount corresponding to a molar $H_2S/H_2$ ratio of between 0.05 and 200.

13. Process according to claim 1, wherein the olefin has the general formula:

$$R_1R_2C{=}CR_3R_4 \qquad (I)$$

in which $R_1$, $R_2$, $R_3$, $R_4$, which are identical or different, represent a hydrogen atom or a linear or branched alkyl radical of 1 to 20 carbon atoms.

14. Process according to claim 1, wherein the olefin used is ethylene.

15. Process according to claim 1, wherein the hydrogen sulphide is introduced in an amount corresponding to a molar $H_2S$/olefin ratio of between 1 and 100.

16. Process according to claim 1, wherein the catalyst composition comprises:
   from 98.5% to 99.9%, by weight of strong acid, and
   from 0.05% to 1.5%, by weight of at least one metal from group VIII.

17. Process according to claim 5, wherein the catalyst composition comprises:
   from 25 to 50%, by weight of strong acid,
   from 0.1% to 2%, by weight of at least one metal from group VIII, and
   from 48% to 75%, by weight of a support selected from silica $SiO_2$, alumina $Al_2O_3$, titanium dioxide $TiO_2$, zirconium oxide $ZrO_2$, and activated carbon.

18. Process according to claim 1, wherein the hydrogen is introduced in an amount corresponding to a molar $H_2S/H_2$ ratio of between 0.1 and 100.

19. Process according to claim 1, wherein the hydrogen sulphide is introduced in an amount corresponding to a molar $H_2S$/olefin ratio of between 2 and 30.

20. Process according to claim 1, wherein the hydrogen sulphide is introduced in an amount corresponding to a molar $H_2S$/olefin ratio of between 4 and 12.

21. Process according to claim 1, wherein n is between 6 and 20.

22. Process according to claim 7, wherein said 12-phosphotungstic acid is impregnated on silica.

23. Process according to claim 13, wherein said linear or branched alkyl radical has 1 to 12 carbon atoms.

* * * * *